United States Patent [19]

Fendler et al.

[11] Patent Number: 5,719,113
[45] Date of Patent: Feb. 17, 1998

[54] ANTIMICROBIAL CLEANSING COMPOSITION CONTAINING CHLORHEXIDINE, AN AMPHOTERIC SURFACTANT, AND AN ALKYL POLYGLUCOSIDE

[75] Inventors: Eleanor J. Fendler, Hudson; Ronald A. Williams, Stow; Michael J. Dolan, Akron, all of Ohio

[73] Assignee: Gojo Industries, Inc., Cuyahoga Falls, Ohio

[21] Appl. No.: 704,135

[22] Filed: Aug. 28, 1996

Related U.S. Application Data

[63] Continuation of Ser. No. 610,677, Mar. 4, 1996, abandoned, which is a continuation of Ser. No. 246,956, May 20, 1994, abandoned.

[51] Int. Cl.$^6$ ............... C11D 1/66; C11D 1/88; C11D 3/26
[52] U.S. Cl. ............ 510/382; 510/123; 510/124; 510/131; 510/132; 510/161; 510/384; 510/470; 510/504; 510/499
[58] Field of Search ................ 510/123, 124, 510/131, 132, 161, 382, 384, 470, 504, 499

[56] References Cited

U.S. PATENT DOCUMENTS

| | | | |
|---|---|---|---|
| 3,855,140 | 12/1974 | Billany et al. | 252/106 |
| 3,960,745 | 6/1976 | Billany et al. | 252/106 |
| 4,196,201 | 4/1980 | Boelle | 424/180 |
| 4,323,468 | 4/1982 | Grollier | 252/174.17 |
| 4,456,543 | 6/1984 | Owens | 252/106 |
| 4,543,205 | 9/1985 | Contamin | 252/546 |
| 4,587,266 | 5/1986 | Verdicchio | 514/635 |
| 4,704,222 | 11/1987 | Smith | 252/106 |
| 4,714,563 | 12/1987 | Kajs et al. | 252/107 |
| 4,748,158 | 5/1988 | Biermann | 514/25 |
| 4,900,721 | 2/1990 | Bansemir et al. | 514/25 |
| 4,919,837 | 4/1990 | Gluck | 252/106 |
| 5,230,835 | 7/1993 | Deguchi | 252/550 |
| 5,234,618 | 8/1993 | Kamegai | 252/106 |
| 5,286,406 | 2/1994 | Scholz | 252/174.17 |
| 5,330,674 | 7/1994 | Urfer | 252/174.17 |
| 5,372,744 | 12/1994 | Kamegai | 252/174.17 |
| 5,422,031 | 6/1995 | Nomura | 252/174.17 |
| 5,449,763 | 9/1995 | Wulff et al. | 536/18.6 |

FOREIGN PATENT DOCUMENTS 0 231 080 A1  1/1987  European Pat. Off. .......... C11D 3/00

*Primary Examiner*—Paul Lieberman
*Assistant Examiner*—Kery A. Fries
*Attorney, Agent, or Firm*—Reese Taylor

[57] ABSTRACT

A cleansing composition includes a salt of chlorhexidine such as chlorhexidine digluconate and at least one nonionic surfactant which does not include any polyoxypropylene/polyoxyethylene block copolymers. Also included in the composition is at least one amphoteric surfactant. Other additives such as viscosifiers or thickeners, emollients, fragrances, perfumes, coloring agents, preservatives, foaming agents, fungicides and the like may also be added. Preferably, the composition does not include alcohol as a carrier. The cleansing composition has been found to exhibit improved antibacterial properties while remaining mild on the skin.

17 Claims, No Drawings

ANTIMICROBIAL CLEANSING COMPOSITION CONTAINING CHLORHEXIDINE, AN AMPHOTERIC SURFACTANT, AND AN ALKYL POLYGLUCOSIDE

This application is a continuation of U.S. patent application Ser. No. 610,677, filed Mar. 4, 1996, now abandoned which is a continuation of U.S. patent application Ser. No. 246,956, filed May 20, 1994 now abandoned.

TECHNICAL FIELD

The present invention relates generally to cleansing compositions. More particularly, the present invention relates to antimicrobial cleansing compositions containing the antibacterial compound chlorhexidine, at least one nonionic surfactant, and at least one amphoteric surfactant. Notably, the antimicrobial cleansing compositions are devoid of any polyoxypropylene/polyoxyethylene block copolymers and any alcohol carriers or diluents. Preferably, the cleansing compositions include specific branched or linear alcohol ethoxylates and/or alkyl polyglucosides as the nonionic surfactant(s).

BACKGROUND OF THE INVENTION

Antibacterial cleansing compositions are widely used in the health care industry by hospital staff and other health care givers, and are particularly suitable for use as preoperative scrubs in surgical practice by hospital personnel such as surgeons, nurses and other health care professionals who might be subject to contact with bacteria and the like prior to operating on a patient. More particularly, these compositions are typically used to cleanse the arms and hands of the user and to destroy bacteria and any other microorganisms which might be present on the user's arms or hands prior to an operation or surgical procedure. These compositions have also been used during surgery to prevent the patient from obtaining bacterial infections and the like.

Heretofore, most antibacterial cleansing compositions essentially contained a bisbiguanide bacterial substance such as chlorhexidine or a salt thereof, at least one surfactant which included a polyoxypropylene/polyoxyethylene block copolymer, and at least one alcohol with or without water as a diluent or carrier. For example, both U.S. Pat. Nos. 3,855,140 and 3,960,745 to Billany et al. disclose cleansing compositions containing a soluble salt of chlorhexidine, a polyoxypropylene/polyoxyethylene block copolymer (a nonionic surfactant), isopropyl alcohol (see Example 1 of both patents) and water. Additional surfactants such as amine oxide foaming agents were also added.

Similarly, European Patent Publication No. 0,231,080 discloses a similar composition to those patented by Billany et al., but includes an aromatic alcohol as a carrier rather than isopropyl alcohol.

In addition, Owens U.S. Pat. No. 4,456,543 teaches an antimicrobial composition which includes three specific polyoxypropylene/polyoxyethylene block copolymers used in conjunction with chlorhexidine or a salt thereof, and water. This particular composition may further include amphoteric surfactants such as cocobetaine, a foam-enhancing amphoteric surfactant, or an amine oxide. A base or acid may also be provided to balance the pH of the composition.

The use of low-foaming nonionic surfactants like polyoxyethylene/polyoxypropylene block copolymers and the like with salts of chlorhexidine, while providing advantageous bactericidal and detergent properties to the composition, nevertheless have to be used at very high concentrations to provide adequate antibacterial activity of chlorhexidine. In fact, as much as 20–25 percent by weight of these block copolymers are necessary to provide sufficient activity for the composition. Moreover, large amounts of these particular nonionic surfactants have been found to be very defatting to the skin. Due to the low-foaming character of nonionic surfactants, amine oxides have been added to provide user acceptability. However, this class of surfactants decreases the antimicrobial efficacy of chlorhexidine salts. Accordingly, the need exists for an antibacterial composition which is suitably effective for killing bacteria and other microorganisms, but which does not include high concentrations of polyoxypropylene/polyoxyethylene block copolymers or amine oxides.

Attempts have been made heretofore to eliminate polyoxypropylene/polyoxyethylene block copolymers from the antimicrobial compositions. For example, Gluck, in U.S. Pat. No. 4,919,837, expressly acknowledges his attempt to lower the quantity of nonionic surfactants in his antiseptic cleansing composition. The essential components of Gluck's composition includes chlorhexidine digluconate, a nonionic surfactant other than polyoxypropylene/polyoxyethylene block copolymers having the formula R—O—(—CH$_2$CH$_2$O—)$_n$H, wherein R is the residue of an alkylphenol or a fatty alcohol and n is a number sufficiently high to assure water solubility between ambient temperatures and 45° C. such as nonylphenolethoxylate, a suitable foaming agent other than an amphoteric surfactant, and a suitable inert diluent or carrier such as water. As noted, Gluck expressly indicates that, in addition to the lack of polyoxypropylene/polyoxyethylene block copolymers, no amphoteric surfactants can be used with his patented composition. However, it is often desirable to have some sort of amphoteric surfactant in the composition to provide enhanced foaming and skin care characteristics to the composition. Moreover, the use of an amphoteric surfactant has been found to destroy a broader spectrum of bacteria than was originally thought possible. The destruction of a broader spectrum of bacteria is seen as a clearly unexpected result in view of the prior art. Furthermore, the addition of amphoteric surfactants permits a lower level of nonionic surfactants to be used, thereby further reducing the possible skin irritation problems which may be associated with some nonionic surfactants.

Still further, the use of nonionic surfactants containing alkylphenol or, more specifically, aromatic alcohol ethoxylates such as nonylphenolethoxylate (a linear or branched phenol ethoxylate) is highly undesirable in view of the toxicity and slow biodegradability of these compounds.

Other patents which may be of interest include Verdicchio U.S. Pat. No. 4,587,266 which relates to the enhancement of antimicrobial activity of bisbiguanide compounds by the addition of amine oxides. Specifically, this patent describes the use of chlorhexidine salts and amine oxides such as amidoamine oxides in aqueous solutions to which hydroxypropyl methyl cellulose may also be added as a thickener.

Smith U.S. Pat. No. 4,704,222 discloses a gelled high-solids aqueous cleaning composition which includes about 25–85 percent particulate abrasive solids, a minor but effective friction-reducing amount of a polysulfonic acid, about 2–35 percent of a plurality of gelling agents, and about 1–10 percent of an anionic surfactant. The composition may also incorporate nonionic surfactants and minor but effective amounts of antimicrobial agents such as chlorhexidine gluconate.

Kajs et al. U.S. Pat. No. 4,714,563 is directed toward antimicrobial toilet bars. These bars include a surfactant selected from soaps, anionic synthetic surfactants and mixtures thereof, and an antimicrobial agent such as chlorhexidine or a salt thereof. However, Kajs et al. particularly point out that highly soluble salts of chlorhexidine such as digluconate are not suitable for use in the patented compositions.

Besides polyoxypropylene/polyoxyethylene block copolymers, antimicrobial compositions also typically employ at least some alcohol as part of the diluent or carrier. For example, Billany et al. U.S. Pat. Nos. 3,855,140 and 3,960,745 indicate the use of isopropyl alcohol while Gluck U.S. Pat. No. 4,919,837 indicates the use of lower alkanols such as ethanol or propanol. However, it is well known that alcohol defats the skin and may cause irritation thereof. Accordingly, an antimicrobial cleansing composition effective against most, if not all, forms of bacteria and microorganisms and having a non-alcoholic carrier, thereby eliminating low molecular weight alcohols in the composition is believed highly desirable.

SUMMARY OF INVENTION

It is therefore an object of the present invention to provide a cleansing composition which effectively kills bacteria and other microorganisms.

It is another object of the present invention to provide a cleansing composition, as above, which is devoid of any polyoxypropylene/polyethylene block copolymers.

It is yet another object of the present invention to provide a cleansing composition, as above, which is devoid of any carriers or diluents containing alcohol.

It is still another object of the present invention to provide a cleansing composition, as above, which includes chlorhexidine or a salt thereof, at least one nonionic surfactant devoid of any aromatic compounds, and at least one amphoteric surfactant.

At least one or more of the foregoing objects, together with the advantages thereof over the known art relating to antimicrobial cleansing compositions, which shall become apparent from the specification which follows, are accomplished by the invention as hereinafter described and claimed.

In general, the present invention provides an antimicrobial cleansing composition including a salt of chlorhexidine; at least one alkyl polyglucoside; and at least one amphoteric surfactant. The composition may also include a non-aromatic nonionic alcohol ethoxylate and is completely devoid of any polyoxypropylene/polyoxyethylene block copolymers. The composition may also be devoid of any carrier containing alcohol.

PREFERRED EMBODIMENT FOR CARRYING OUT THE INVENTION

The present invention is directed toward an antibacterial cleansing composition which effectively kills bacteria and other microorganisms, but is otherwise mild on the skin such that it does not cause skin irritation or dryness. That is, the antimicrobial cleansing compositions of the present invention have been found to reduce significantly the number of colony forming units (cfu's) of bacteria such as *Staphylococcus aureus* and the like and to do so without the use of lower alcohols or polyoxypropylene/polyoxyethylene block polymers.

The essential ingredients for such an antimicrobial cleansing composition generally includes a salt of chlorhexidine, at least one nonionic surfactant, and at least one amphoteric surfactant. These ingredients, along with other additives disclosed hereinbelow, provide compositions with excellent disinfecting properties as well as excellent cleansing properties.

As is generally known in the art, the antibacterial activity for the compositions is generally provided by the salt of chlorhexidine found therein. Preferably, these salts of chlorhexidine are soluble in non-alcoholic solvents and are used in amounts ranging from about 0.2 to 5 percent by weight of the total composition, with about 2 to 4 percent by weight of the total composition being most preferred. Any salt of chlorhexidine which is soluble in water or other non-alcohol solvent, e.g., gluconate, acetate, formate, lactate, isethionate, succinamate, glutamate, mono-diglycollate, dimethanesulfonate, di-isobutyrate, glucoheptonate, etc., may be used in the compositions of the present invention. However, the preferred chlorhexidine salts are gluconate and acetate.

The most preferred salt is chlorhexidine digluconate (CHG). CHG is an effective antibacterial agent suitable for use as a cleansing composition due to its low toxicity and mildness on the skin. In the examples presented hereinbelow, CHG is the only chlorhexidine salt presented therein. However, the present invention should not necessarily be limited to this particular chlorhexidine salt as other salts may also be suitable for the purposes of the present invention.

As noted hereinabove, at least one nonionic surfactant is also incorporated into the composition of the present invention. However, the use of some nonionic surfactants with chlorhexidine have been found to substantially reduce the antibacterial activity of the chlorhexidine. Accordingly, only particular nonionic surfactants may be employed. Moreover, as noted hereinabove, some of the nonionic surfactants which do not completely eliminate the antibacterial activity of chlorhexidine have significant other problems which limit their use or desirability. For example, no polyoxypropylene/polyoxyethylene block copolymers should be used, thereby reducing skin irritation and possible sudsing problems associated with these compounds, and no aromatic alcohol ethoxylates should be used, thereby eliminating the toxicity and slow biodegradability problems associated with those ethoxylates.

In order to overcome these problems, the composition of the present invention preferably includes at least one alkyl polyglucoside as at least one nonionic surfactant. In addition, a second nonionic surfactant may be selected from the group consisting of branched alcohol ethoxylates or linear alcohol ethoxylates. More particularly, the cleansing composition of the present invention preferably includes either an alkyl polyglucoside, or a branched or linear alcohol ethoxylate and an alkyl polyglucoside. Thus, it will be appreciated that the amount of nonionic surfactant(s) to be added to the composition is somewhat dependent upon the number of nonionic surfactants added. However, the amount of all of the nonionic surfactants together generally will not comprise more than about 20 percent by weight of the total composition.

With respect to the alkyl polyglucosides (APG), any APG which meets the objects of the present invention and is suitable for incorporation into the present composition may suffice. APGs having an alkyl chain length of from about $C_8$ to about $C_{16}$ are preferred and have been found to be most effective for the present invention, although other chain lengths are not necessarily precluded and may fall within the scope of the present invention. Preferably, APG is employed in the compositions of the present invention in amounts ranging from a minor, but effective amount to about 10 percent by weight of the total composition with about 4 to 6 percent by weight being most preferred.

As noted hereinabove, any APG may be suitable for the present invention. In fact, blends of more than one APG may be used as a nonionic surfactant. For example, as shown in Table VIII hereinbelow, one of the most preferred APGs is a blend of APG 200 and APG 400 both of which are available from Henkel Corp. of Hoboken, N.J. It is believed that APG-400 is also a blend in itself as manufactured by Henkel Corp. Consequently, it will be appreciated that any APG, whether blended or directly manufactured, is suitable for the present invention so long as it accomplishes the objects set forth hereinabove. Other examples of APGs found to be suitable for the present invention include those available from Henkel Corp. of Hoboken, N.J., under the tradenames Plantaren or Glucopon, as well as those available from Seppic of Paris, France, under the tradename Oramix NS 10. These compounds are seen as being particularly effective in use with CHG and do not significantly reduce the antibacterial activity of the chlorhexidine, especially when used with the amphoteric surfactants detailed hereinbelow, and have been found to be extremely effective with CHG in killing Staphylococcus aureus and other microorganisms as detailed hereinbelow.

When branched or linear alcohol ethoxylates are employed, they are preferably incorporated in amounts ranging from 0 (absent) to about 10 percent by weight of the total composition, with a range of from about 1 to 3 percent by weight being most preferred. These alcohol ethoxylates preferably have alkyl hydrophobes of less than 14 carbon atoms and include only those branched or linear alcohol ethoxylates which are known to or can be proven to be effective against bacteria and the like because they do not destroy the bactericidal activity of the chlorhexidine.

One example of a branched alcohol ethoxylate which is particularly suited for the purposes of the present invention is tridecylalcohol ethoxylate (EO=10). This alcohol ethoxylate is also commonly referred to as polyoxyethylene (10) tridecanol, and is available from Rhone-Poulenc, Inc. under the tradename Rhoadsurf BC-720. Tridecylalcohol ethoxylate is the only branched alcohol ethoxylate known to date to produce the effective results desired for the composition of the present invention. However, all branched alcohol ethoxylates which effectively kill bacteria and other microorganisms and which do not significantly hinder the antibacterial activity of the chlorhexidine should also be considered suitable and fall within the scope of the present invention.

An example of a linear alcohol ethoxylate suitable for the present composition is linear $C_{9-11}$ alcohol ethoxylate (EO=8), also referred to as polyoxyethylene (8) linear $C_{9-11}$ alkanol. This linear alcohol ethoxylate is available from Shell Chemical Co. of Houston, Tex., under the trademark Neodol 91-8. Other linear alcohol ethoxylates which are known to be particularly suitable for the present invention and do not significantly hinder the antibacterial activity of the chlorhexidine include linear $C_{10}$ alcohol ethoxylate (EO=4), also referred to as polyoxyethylene (4) linear $C_{10}$ alkanol and sold under the tradename Rhoadsurf DA-530 (Rhone-Poulenc) and linear $C_{10}$ alcohol ethoxylate (EO=6), also referred to as polyoxyethylene (6) linear $C_{10}$ alkanol and sold under the tradename Rhoadsurf DA-630 (Rhone-Poulenc). Although less preferable, still other linear alcohol ethoxylates which can be used, although they are known to be somewhat less effective, include linear $C_{9-11}$ alcohol ethoxylate (EO=6), also referred to as polyoxyethylene (6) linear $C_{9-11}$ alkanol and sold under the trademark Neodol 91-6 (Shell Chemical); linear $C_{11}$ alcohol ethoxylate (EO=3), also referred to as polyoxyethylene (3) linear $C_{11}$ alkanol and sold under the trademark Neodol 1-3 (Shell Chemical); linear $C_{11}$ alcohol ethoxylate (EO=5), also referred to as polyoxyethylene (5) linear $C_{11}$ alkanol and sold under the trademark Neodol 1-5 (Shell Chemical); linear $C_{11}$ alcohol ethoxylate (EO=7), also referred to as polyoxyethylene (7) linear $C_{11}$ alkanol and sold under the trademark Neodol 1-7 (Shell Chemical); linear $C_{12-13}$ alcohol ethoxylate (EO=6.5), also referred to as polyoxyethylene (6.5) linear $C_{12-13}$ alkanol and sold under the trademark Neodol 23-6.5 (Shell Chemical); linear $C_{8-10}$ alcohol ethoxylate (EO=2), also referred to as polyoxyethylene (2) linear $C_{8-10}$ alkanol and sold under the trademark Alfonic 810-60 (Vista Chemical Co., Houston, Tex.); linear $C_{10-12}$ alcohol ethoxylate (EO=6), also referred to as polyoxyethylene (6) linear $C_{10-12}$ alkanol and sold under the trademark Alfonic 1012-60 (Vista Chemical); linear $C_8$ alcohol ethoxylate (EO=5), also referred to as polyoxyethylene (5) linear $C_8$ alkanol and sold under the tradename Poly-Tergent SL-42 (Olin); and linear $C_8$ alcohol ethoxylate (EO=8), also referred to as polyoxyethylene (8) linear $C_8$ alkanol and sold under the tradename Poly-Tergent SL-62 (Olin).

Each of these alcohol ethoxylates have been found not to effect severely the antibacterial activity of chlorhexidine. In fact, the most preferred linear alcohol ethoxylates, Neodol 91-8, Rhoadsurf DA-530 and Rhoadsurf DA-630, have been found to provide even better antibacterial activity than when CHG is used by itself. Moreover, these alcohol ethoxylates are devoid of alkylphenol compounds and other aromatic alcohols.

The antibacterial cleansing compositions of the present invention also include at least one amphoteric surfactant. The amphoteric surfactant is believed not only to provide better foaming properties, but also helps to enhance the antibacterial activity of the chlorhexidine by providing the composition with the capability of destroying a broader spectrum of bacteria. The amount of amphoteric surfactant to be added to the composition typically depends upon the number and type of amphoteric surfactant(s) used. However, in general, these surfactants are preferably incorporated into the composition in amounts ranging from a minor, but effective amount to about 10 percent by weight, with about 0.25 to 6 percent of the total composition being most preferred.

Amphoteric surfactants used in the cleansing compositions of the present invention may include, but are not necessarily limited to, phospholipids. One class of phospholipids suitable for the present invention include alkyl phosphatidyl PG-dimonium chloride. Preferred alkyl phosphatidyl PG-dimonium chlorides are cocoamidopropyl phosphatidyl PG-dimonium chloride, a phospholipid available from MONA Industries, Inc. of Paterson, N.J., under the tradename Phospholipid PTC; stearamidopropyl phosphatidyl PG-dimonium chloride, available from MONA under the tradename Phosphdipid PTS; linoleamidopropyl phosphatidyl PG-dimonium chloride, available from MONA under the tradename Phospholipid EFA; and stearamidopropyl phosphatidyl PG-dimonium chloride/cetyl alcohol, available from MONA under the trade name Phospholipid SV. Preferably, such compounds are incorporated into the composition in an amount ranging from 0 (absent) to about 5 percent by weight of the total composition.

When APG is employed without any of the other nonionic surfactants, another amphoteric surfactant is preferably added. Specifically, up to 10 percent by weight of the total composition of an alkylammonio carboxylate having from 8 to 18 carbon atoms may be incorporated into the composition. One such alkylammonio carboxylate is cocobetaine, and is available from McIntyre Chemical Co. of Chicago, Ill., under the tradename Mackam CB-35.

The composition may also include other additives such as thickeners, emollients, foaming agents, fragrances, coloring agents, preservatives, fungicides, opacifying agents, pearlizing agents, vitamins, and the like. For example, the composition may include a polymer viscosifier or thickener such as hydroxyethyl cellulose to make the composition more useful. Examples of other suitable polymer viscosifiers include, but are not necessarily limited to, hydroxypropyl cellulose, methyl cellulose, and carboxymethyl cellulose. These viscosifiers may be added in amounts ranging from 0 (absent) to about 2 percent by weight of the total composition.

A glycol may be added as an emollient. Preferred glycols include propylene glycol, triethylene glycol, and hexylene glycol, with propylene glycol being most preferred. These glycols may be added in amounts ranging from 0 (absent) to about 10 percent by weight of the total composition, with about 3 percent being most preferred.

A foam-enhancing agent in addition to the amphoteric surfactant and/or a quaternary ammonium surfactant may also be added to the composition. For example, as is well known in the art, amine oxides may be added to provide even better sudsing properties to the composition. Although generally all quaternary ammonium surfactants can be employed, one example of a quaternary ammonium surfactant suitable for use with the present invention is didecyldimethyl ammonium chloride, such as is presently available from Lonza under the trademark Bordac® 2250. These compounds are preferably added in amounts ranging from 0 (absent) to about 10 percent by weight of the total composition.

The composition of the present invention may further comprise minor but effective amounts of other conventional additives such as fungicides, fragrances, preservatives, color additives, opacifying agents, pearlizing agents, vitamins, etc. An example of a particular effective fungicide suitable for use with the present invention is dimethyl oxazolidine, available from Angus under the tradename Oxaban A. An example of a particular pearlizing agent is ethylene glycol distearate pearl. Generally, these additives are used in amounts which do not affect the essential nature of the composition.

For optimal antibacterial efficacy, the pH of the composition should be between 5.5 and 8, and preferably between 6.5 and 7.5. To adjust the pH of the composition, any acid compatible with the components of the composition can be used. Preferred acids include lactic acid, acetic acid, glycolic acid, gluconic acid, and citric acid, with the first three acids being most preferred. A pH of greater than 8 typically causes degradation of the chlorhexidine free base. Typically, less than 1 percent by weight of these acids are used to achieve the proper pH.

The balance of the composition is typically water or other non-alcohol solvent so as to provide 100 percent by weight of the composition. Preferably, no alcohol solvent is used; although, if alcohol were used, it would not materially affect the nature of the composition other than in ways previously disclosed hereinabove.

All percents by weight indicated herein are based upon the percent active composition. Thus, for example, where 2 percent by weight CHG is employed and the CHG is obtained from the manufacturer in a 20 percent active solution, 10 percent of the solution will have to be used in order to obtain the 2 percent by weight recommended.

The antimicrobial cleansing compositions of the present invention are generally prepared by dissolving the various ingredients such as the soluble salt of chlorhexidine, the nonionic surfactant(s), and the amphoteric surfactant(s) in water. More particularly, alkyl polyglucoside or other suitable surfactant, amphoteric surfactant(s), propylene glycol, fungicide, and other ingredients (fragrance and pearlizing agent, etc.) are dissolved in water with stirring. Lactic acid is added followed by the CHG. The viscosifier is then preferably added and the solution is mixed until it is completely hydrated. The pH is checked and adjusted with lactic acid or sodium hydroxide if necessary. This process can be employed with or without the application of heat to enhance dissolution.

In order to demonstrate practice of the present invention, several antimicrobial cleansing compositions were prepared according to the concepts of the present invention as presented hereinabove and were tested to determine their effectiveness against at least one strain of the particular bacteria, *Staphylococcus aureus*. This particular strain is on deposit with and is available to the scientific public from the American Type Culture Collection (ATCC), Rockville, Md., under Accession No. 33591. The compositions of the present invention may, where indicated below, have also been studied with respect to other strains of *Staphylococcus aureus*, also available to the scientific public from the ATCC under various Accession numbers as well as other types of bacteria such as at least one strain of *Serratia marcescens*, available to the scientific public from the ATCC under the Accession No. 14756 and at least one strain of *Escherichia coli*, available to the scientific public from the ATCC under the Accession No. 8739.

Initially, however, various compositions were prepared from 2 percent by weight CHG (20% active), 2 or 6 percent by weight of an nonionic surfactant, and the balance, water. The pH of the composition was determined and adjusted to 5.5. The nonionic surfactants used were a variety of branched or linear alcohol ethoxylates. The compositions were then subjected to a thirty-second kill study of the challenge bacteria, namely *Staphylococcus aureus* (ATCC Accession No. 33591). For this test, ten milliliter samples of the test solutions were placed into sterile 30 ml beakers containing a magnetic stir bar. The beaker with the test sample was placed onto a magnetic stirrer and approximately 10 to 15 seconds prior to inoculating the test sample with the challenge bacteria, the stirrer was turned on to allow good mixing without addition of air into the sample. One hundred microliters (µl) of challenge bacteria was introduced into the sample at time 0 and allowed to mix for approximately 20 seconds. Two hundred-fifty µl of the challenged sample was removed with a 250 µl positive displacement pipettor and dispensed at 30 seconds into 24.74 ml of neutralizing broth (2 percent tryptic soy broth (TSB), 10 percent Polysorbate 80, 4 percent Polysorbate 20, 0.75 percent Lecithin, 0.5 percent Dextrose, and 82.75 percent Distilled Water) and mixed well. Serial dilutions were made by standard methods well known in the art and plated into pour plates with tryptic soy agar (TSA) containing Polysorbate 80 and Lecithin (available from BBL). The plates were incubated at 35° C. for 48 hours and plates containing 30–300 colonies were counted. The challenge bacterial suspension was enumerated as were the test solutions using 10 ml of Sterile Distilled Water as the test solution.

The test results were used to determine which branched or linear alcohol ethoxylates could be used in formulations of the present invention. Table I, presented hereinbelow, shows the efficacy of reduction of colony forming units (cfu's) of *Staphylococcus aureus* (ATCC Accession No. 33591) for several compositions having different branched or linear alcohol ethoxylates in water with 2 percent by weight CHG and 4 percent by weight isopropyl alcohol, and the alkyl hydrophobe of each alcohol ethoxylate. The efficacy results have been calculated on a log scale in order to provide a better understanding of the significant improvement in effectiveness on bacteria certain alcohol ethoxylates have as compared to other alcohol ethoxylates. In percentages, efficacy is considerably less clear insofar as many of these compositions reduce the number of cfu's by greater than 99 percent (a 2 log reduction).

TABLE I

NONIONIC ALCOHOL ETHOXYLATES EFFICACY STUDY THIRTY SECOND KILL STUDY AGAINST *Staphylococcus aureus* (ATCC 33591)

| ALCOHOL ETHOXYLATE (TRADENAME) | SURFACTANT EFFICACY LOG REDUCTION | | ALKYL HYDROPHOBE |
|---|---|---|---|
| | 6% | 2% | |
| Rhone-Poulenc | | | |
| Rhoadsurf BC-720 | >5.57 | >5.59 | Branched $C_{13}$ |
| Rhoadsurf DA-530 | >5.66 | >5.66 | $C_{10}$ |
| Rhoadsurf DA-630 | >5.66 | 5.48 | $C_{10}$ |
| Rhoadsurf ON-870 | 1.76 | 2.70 | Oleyl |
| Alkamuls EL-719 | 1.28 | 1.59 | Caster Oil |
| Alkamuls EL-620 | 1.35 | 1.98 | Caster Oil |
| Shell | | | |
| Neodel 1-3 | PS* | 5.54 | $C_{11}$ |
| Neodel 1-5 | 4.41 | 4.54 | $C_{11}$ |
| Neodel 1-7 | 3.54 | 3.33 | $C_{11}$ |
| Neodel 1-9 | 2.66 | =1.78 | $C_{11}$ |
| Neodel 91-8 | 4.09 | >5.28 | $C_9-C_{11}$ |
| Neodel 91-6 | 3.15 | 2.45 | $C_9-C_{11}$ |
| Neodel 23-6.5 | 3.29 | 2.77 | $C_{12}-C_{13}$ |
| Neodel 25-7 | 2.23 | =1.84 | $C_{12}-C_{15}$ |
| Neodel 25-9 | <1.93 | <1.93 | $C_{12}-C_{15}$ |
| Neodel 25-12 | <1.93 | <1.93 | $C_{12}-C_{15}$ |
| Neodel 45-7 | <1.66 | <1.66 | $C_{14}-C_{15}$ |
| Neodel 45-13 | <1.93 | <1.93 | $C_{12}-C_{15}$ |
| Vista | | | |
| Alfonic 810-60 | >5.63 | 3.94 | $C_8-C_{10}$ |
| Alfonic 1012-60 | 2.78 | 2.42 | $C_{10}-C_{12}$ |
| Alfonic 1214-70 | <1.66 | <1.66 | $C_{12}-C_{14}$ |
| Alfonic 1218-70 | <1.66 | <1.66 | $C_{12}-C_{18}$ |
| Alfonic 1412-60 | <1.93 | <1.93 | $C_{12}-C_{14}$ |
| Alfonic 1412-66 | <1.93 | <1.93 | $C_{12}-C_{14}$ |
| Alfonic 1412-70 | <1.93 | <1.93 | $C_{12}-C_{14}$ |
| Alfonic 1618-65 | <1.66 | <1.66 | $C_{16}-C_{18}$ |
| Hoechst-Celanese | | | |
| Genapol 24-L-60 | <1.93 | <1.93 | $C_{12}-C_{14}$ {Synthetic} |
| Genapol 24-L-98 | <1.93 | <1.93 | $C_{12}-C_{14}$ {Synthetic} |
| Genapol 26-L-60 | <1.93 | <1.93 | $C_{12}-C_{16}$ {Natural} |
| Genapol 26-L-98 | <1.93 | <1.93 | $C_{12}-C_{16}$ {Natural} |
| Olin | | | |
| Poly-Tergent SL-42 | 4.34 | 3.72 | $C_8$ |
| Poly-Tergent SL-62 | 3.23 | 2.44 | $C_8$ |
| Poly-Tergent SL-92 | <1.96 | 3.58 | $C_8$ |

*Partially Soluble

As shown in Table I, it is apparent that at least one branched alcohol ethoxylate (Rhoadsurf BC-720) and at least three linear alcohol ethoxylates (Rhoadsurf DA-530, Rhoadsurf DA-630 and Neodol 91-8) do not reduce the antibacterial activity of chlorhexidine at all and may well, in fact, effectively increase the antibacterial activity of chlorhexidine or act as an adjunct for destroying bacteria such as *Staphylococcus aureus*. These nonionic alcohol ethoxylates are shown in Table I to reduce the number of surviving cfu's so significantly that the log reduction value for these ethoxylates is greater than 5 where only about 2 percent by weight of the surfactant is employed. Generally, although not shown, it has been found that CHG in water will effectively reduce the number of surviving cfu's only to a log reduction value of about 3.2. Thus, by simply adding these particular branched or linear alcohol ethoxylates, the bactericidal efficacy of the CHG is either enhanced by the alcohol ethoxylates, or the alcohol ethoxylates add to the effectiveness of the composition to destroy bacteria. In addition, it is noted that one other linear alcohol ethoxylate, Neodol 1-3, also was extremely effective (has a log value greater than 5 at about 2 percent by weight) against this strain of *Staphylococcus aureus*, but was only partially soluble in water when used in an amount of about 6 percent by weight.

Furthermore, from Table I, it is evident that still other nonionic alcohol ethoxylates appear not to reduce significantly the antibacterial activity of the CHG, but are not nearly as effective as the alcohol ethoxylates noted hereinabove. Nevertheless, it appears as if Neodol 1-5, Neodol 1-7, Alfonic 810-60 and Poly-Tergent SL-42 may also be effective in destroying a substantial amount of this type of bacteria. Based upon this data, it is also believed that Neodol 91-6, Neodol 23-6.5, Alfonic 1012-60 and Poly-Tergent SL-62 may be somewhat effective in destroying certain types of bacteria.

Next, seven compositions (1 through 7, inclusive) were prepared using all of the essential ingredients of the present invention except an amphoteric surfactant. Such compositions are seen as being somewhat similar to those presented in Gluck U.S. Pat. No. 4,919,837, although they are not the same insofar as no alkylphenol or other aromatic alcohol ethoxylates were used. In particular, the compositions included a soluble salt of chlorhexidine, namely chlorhexidine digluconate (about 2 percent by weight); two nonionic surfactants, namely an alkyl polyglucoside (about 3–5 percent by weight APG) and a branched or linear alcohol ethoxylate (about 3–5 percent by weight); but no amphoteric surfactant. Additives such as glycol emollients (propylene glycol), thickeners (hydroxyethyl cellulose) and, in one instance, a fragrance were also added. The compositions were adjusted to a pH of 5.5. The balance of the composition was water to provide 100 percent by weight of the total composition.

For each of these seven compositions, a different alcohol ethoxylate was added. Table II presented hereinbelow shows the compositional make-up of each of the examples tested, and Table III reports the efficacy log reduction results of the various thirty-second kill studies performed against *Staphylococcus aureus* (ATCC Accession No. 33591), *Escherichia coli* (ATCC Accession No. 8739), *Escherichia coli* (ATCC Accession No. 11229), *Serratia marcescens* (ATCC Accession No. 14756), and/or *Pseudomonas aeruginosa* (ATCC Accession No. 15442). As can be seen in the Table III, for compositions 4–7, a thirty second kill study was performed against only *Staphylococcus aureus* (ATCC Accession No. 33591). It is believed that if the composition is effective against this bacteria, then it would be suitably effective against the other types of bacteria.

TABLE II

ANTIMICROBIAL CLEANSING FORMULATIONS WITHOUT AN AMPHOTERIC SURFACTANT

| INGREDIENTS {tradename} | COMPOSITIONS (PERCENT BY WEIGHT) | | | | | | |
|---|---|---|---|---|---|---|---|
| | 1 | 2 | 3 | 4 | 5 | 6 | 7 |
| Chlorhexidine Gluconate (20% active) | 2.0 | 2.0 | 2.0 | 2.0 | 2.0 | 2.0 | 2.0 |
| Hydroxyethyl cellulose {Natrosol 250 HHR} | 0.7 | 0.7 | 0.7 | 0.7 | 0.7 | 0.7 | 0.7 |
| Propylene Glycol-USP | 3.0 | 3.0 | 3.0 | 3.0 | 3.0 | 3.0 | 3.0 |
| APG (50% active) | 3.0 | 5.0 | 5.0 | 3.0 | 3.0 | 3.0 | 3.0 |
| Polyoxyethylene (10) tridecanol (Tridecylalcohol ethoxylate [EO = 10]) {Rhoadsurf BC-720} | 3.0 | — | — | — | — | — | — |
| Polyoxyethylene (4) Linear $C_{10}$ alkanol (Linear $C_{10}$ alcohol ethoxylate [EO = 4]) {Rhoadsurf DA-530} | — | 3.0 | — | — | — | — | — |
| Polyoxyethylene (6) Linear $C_{10}$ alkanol (Linear $C_{10}$ alcohol ethoxylate [EO = 6]) {Rhoadsurf DA-630} | — | — | 3.0 | — | — | — | — |
| Polyoxyethylene (8) Linear $C_{9-11}$ alkanol (Linear $C_{9-11}$ alcohol ethoxylate [EO = 8]) {Neodol 91-8} | — | — | — | 5.0 | — | — | — |
| Polyoxyethylene (6) Linear $C_{9-11}$ alkanol (Linear $C_{9-11}$ alcohol ethoxylate [EO = 6]) {Neodol 91-6} | — | — | — | — | 5.0 | — | — |
| Polyoxyethylene (2) Linear $C_{8-10}$ alkanol (Linear $C_{8-10}$ alcohol ethoxylate [EO = 2]) {Alfonic 810-60} | — | — | — | — | — | 5.0 | — |
| Polyoxyethylene (6) Linear $C_{10-12}$ alkanol (Linear $C_{10-12}$ alcohol ethoxylate [EO = 6]) {Alfonic 1012-60} | — | — | — | — | — | — | 5.0 |
| Fragrance | 0.1 | — | — | — | — | — | — |
| pH Adjustment to 5.5 + Water | balance to provide 100 percent by weight | | | | | | |

TABLE III

ANTIBACTERIAL EFFICACY SCREEN THRITY SECOND KILL STUDY OF STRAINS OF BACTERIA FOR COMPOSITIONS CONTAINING NONIONIC ALCOHOL ETHOXYLATES

| COMPOSITION | BACTERIA | | | | |
|---|---|---|---|---|---|
| | Staphylococcus aureus (33591) | Escherichia coli (8739) | Escherichia coli (11229) | Serratia marcescens (14756) | Pseudomonas aeruginosa (15442) |
| 1 | >5.3512 | >5.2095 | >5.2393 | >5.6263 | — |
| 2 | >5.4409 | >5.2443 | — | >5.7782 | >5.4440 |
| 3 | >5.4409 | >5.2443 | — | >5.7782 | >5.4440 |
| 4 | >5.7018 | — | — | — | — |
| 5 | >5.7018 | — | — | — | — |
| 6 | 5.3496 | — | — | — | — |
| 7 | 4.2953 | — | — | — | — |

As shown in Table III, each of the seven compositions were determined to be effective against the type(s) of bacteria each composition was intended to destroy. In fact, Compositions 1–6 produced high efficacy reduction results having log values of more than 5. While Composition 7 did not have as high efficacy results as the former six compositions, it did perform suitably well and beyond what would be expected with only CHG and water.

Nevertheless, like CHG and water, Compositions 1 through 7 do not have adequate sudsing or foaming properties expected from cleansing compositions of this type. Accordingly, it was seen as necessary to include an amphoteric surfactant to enhance the foaming properties of the composition. It has been found that adding an amphoteric surfactant also provides for the effective destruction of a broader range of bacteria than is typically considered possible when no amphoteric surfactant is used.

Thus, twelve more compositions (8 through 19, inclusive) were prepared using all of the essential ingredients of the present invention and according to the present invention as detailed hereinabove. Specifically, the compositions included a soluble salt of chlorhexidine, namely chlorhexidine digluconate (about 2 percent by weight); a nonionic surfactant, namely one of three alkyl polyglucosides (about 6 percent by weight APG) selected from certain APGs available from Henkel Corp.; and two amphoteric surfactants, namely, cocobetaine (about 2 percent by weight) and cocoamidopropyl phosphatidyl PG-dimonium chloride (about 0.25 percent by weight). Additives such as glycol emollients (propylene glycol), thickeners (hydroxyethyl cellulose) and fragrances were also added. Four trials of each composition having differing APGs were prepared with each of the four trial compositions for each APG being adjusted to a pH of 6.5, 7.0, 7.5 and 8.0 respectively. This was done by using lactic acid. The balance of the composition was water to provide 100 percent by weight of the total composition. Similarly, a control, shown as Composition 20, was prepared using substantially the same techniques, but the control composition included no APG or amphoteric surfactant.

Table IV presents the compositional formulations of each of the compositions 8–20 tested, and Table V reports the efficacy in terms of log reduction for a thirty-second kill study performed against Staphylococcus aureus (ATCC Accession No. 33591) hereinbelow.

the compositions made according to the present invention. Thus, it should be evident that the relatively mild compositions of the present invention are effective in destroying

TABLE IV

ANTIMICROBIAL CLEANSING FORMULATIONS

| INGREDIENT {tradename} | COMPOSITION (PERCENT BY WEIGHT) | | | | | | |
|---|---|---|---|---|---|---|---|
| | 8 | 9 | 10 | 11 | 12 | 13 | 14 |
| Chlorhexidine Gluconate (20% active) | 2 | 2 | 2 | 2 | 2 | 2 | 2 |
| Hydroxyethyl cellulose {Natrosol 250 HHR} | .7 | .7 | .7 | .7 | .7 | .7 | .7 |
| Propylene Glycol-USP | 3 | 3 | 3 | 3 | 3 | 3 | 3 |
| APG-300 (50% active) | 6 | 6 | 6 | 6 | — | — | — |
| APG-425 (50% active) | — | — | — | — | 6 | 6 | 6 |
| APG-325 (50% active) | — | — | — | — | — | — | — |
| Cocobetaine ($C_{12-14}$ alkylammonio carboxylate) {Mackam CB-35} (35% active) | 2 | 2 | 2 | 2 | 2 | 2 | 2 |
| Cocoamidopropyl phosphatidyl PG-dimonium chloride {Phospholipid PTC} (47% active) | .25 | .25 | .25 | .25 | .25 | .25 | .25 |
| Lactic Acid - USP (88%) | .09 | .09 | .09 | .09 | .09 | .09 | .09 |
| Fragrance | .1 | .1 | .1 | .1 | .1 | .1 | .1 |
| pH | 6.5 | 7.0 | 7.5 | 8.0 | 6.5 | 7.0 | 7.5 |
| Deionized Water | balance to provide 100 percent by weight | | | | | | |

| INGREDIENT {tradename} | COMPOSITION (PERCENT BY WEIGHT) | | | | | |
|---|---|---|---|---|---|---|
| | 15 | 16 | 17 | 18 | 19 | Control 20 |
| Chlorhexidine Gluconate (20% active) | 2 | 2 | 2 | 2 | 2 | 2 |
| Hydroxyethyl cellulose {Natrosol 250 HHR} | .7 | .7 | .7 | .7 | .7 | .7 |
| Propylene Glycol-USP | 3 | 3 | 3 | 3 | 3 | 3 |
| APG-300 (50% active) | — | — | — | — | — | — |
| APG-425 (50% active) | 6 | — | — | — | — | — |
| APG-325 (50% active) | — | 6 | 6 | 6 | 6 | — |
| Cocobetaine ($C_{12-14}$ alkylammonio carboxylate) {Mackam CB-35} | 2 | 2 | 2 | 2 | 2 | — |
| Cocoamidopropyl phosphatidyl PG-dimonium chloride {Phospholipid PTC} | .25 | .25 | .25 | .25 | .25 | — |
| Lactic Acid - USP (88%) | .09 | .09 | .09 | .09 | .09 | — |
| Fragrance | .1 | .1 | .1 | .1 | .1 | — |
| pH | 8.0 | 6.5 | 7.0 | 7.5 | 8.0 | 7.0 |
| Deionized Water | balance to provide 100 percent by weight | | | | | |

TABLE V

ANTIBACTERIAL EFFICACY SCREEN
THIRTY SECOND KILL STUDY AGAINST Staphylococcus arureus
(ATCC #33591)

| COMPOSITION | LOG REDUCTION |
|---|---|
| 8 | >5.293 |
| 9 | >5.2934 |
| 10 | >5.2934 |
| 11 | >5.2934 |
| 12 | 4.5944 |
| 13 | 4.7493 |
| 14 | 5.1173 |
| 15 | >5.2934 |
| 16 | >5.2934 |
| 17 | >5.2934 |
| 18 | >5.2934 |
| 19 | >5.2934 |
| 20 (control) | 2.3489 |

As can be seen in the Table V, the specific type of APG employed had only a minor effect on the antibacterial performance of the compositions. Nevertheless, the same cannot be said for the control composition. As shown, when no APG or amphoteric surfactant are employed, the efficacy log reduction was found to be only about 2.3. This is significantly less than the log reduction values obtained for bacteria as well as or even better than compositions which do not include APG or amphoteric surfactants.

Continuing, eight more compositions (21 through 28, inclusive) were prepared according to the present invention and using all of the essential ingredients of the present invention as detailed hereinabove. More particularly, the compositions included a soluble salt of chlorhexidine, namely chlorhexidine digluconate (about 2 percent by weight); a nonionic surfactant, namely an alkyl polyglucoside (about 4–6 percent by weight APG); and two amphoteric surfactants, namely, cocobetaine (about 2 percent by weight) and cocoamidopropyl phosphatidyl PG-dimonium chloride (about 0.25 percent by weight). Additives such as glycol emollients (propylene glycol), thickeners (hydroxyethyl cellulose) and fragrances were also added. Compositions 21–23, inclusive, were prepared in the same manner as were Compositions 8–19, but each composition was adjusted to a pH of 6.0, 6.5, and 7.0, respectively. Compositions 24–26, inclusive, also were adjusted to a pH of 6.0, 6.5, and 7.0, respectively, but included acetic acid rather than lactic acid. Compositions 27 and 28 were prepared in the same manner as Composition 25 (including pH=6.5), but had less APG, 5 percent and 4 percent by weight, respectively. Water was substituted for the loss in APG and constituted the balance of the composition to total 100 percent by weight. Similarly, a control, shown as Composition 29, was prepared using substantially the same techniques as above for Composition 20, but again, the control composition included no APG or amphoteric surfactant.

Table VI hereinbelow presents the compositional formulations of each of the compositions 21–29 tested, and Table VII reports the efficacy in terms of log reduction for a thirty-second kill study performed against *Staphylococcus aureus* (ATCC Accession No. 33591).

chlorhexidine, namely CHG (about 2 percent by weight); a nonionic surfactant, namely a blend of different portions of two known alkyl polyglucosides (totaling about 6 percent by weight) available from Henkel Corp., and two amphoteric surfactants, namely cocobetaine (about 2 percent by weight) and cocoamidopropyl phosphatidyl PG-dimonium chloride (about 0.25 percent by weight). Additives such as glycol emollients (propylene glycol), viscosifiers (hydroxyethyl cellulose), fungicides, fragrances, and pearlizing agents

TABLE VI

ANTIMICROBIAL CLEANSING FORMULATIONS

| | COMPOSITION (PERCENT BY WEIGHT) | | | | | | | | |
|---|---|---|---|---|---|---|---|---|---|
| INGREDIENT {tradename} | 21 | 22 | 23 | 24 | 25 | 26 | 27 | 28 | Control 29 |
| Chlorhexidine Gluconate (20% active) | 2 | 2 | 2 | 2 | 2 | 2 | 2 | 2 | 2 |
| Hydroxyethyl cellulose {Natrosol 250 HHR} | .7 | .7 | .7 | .7 | .7 | .7 | .7 | .7 | .7 |
| Propylene Glycol-USP | 3 | 3 | 3 | 3 | 3 | 3 | 3 | 3 | 3 |
| APG-300 (50% active) | 6 | 6 | 6 | 6 | 6 | 6 | 5 | 4 | — |
| Cocobetaine ($C_{12-14}$ alkylammonio carboxylate) {Mackam CB-35} (35% active) | 2 | 2 | 2 | 2 | 2 | 2 | 2 | 2 | — |
| Cocoamidopropyl phosphatidyl PG-dimonium chloride {Phospholipid PTC} (47% active) | .25 | .25 | .25 | .25 | .25 | .25 | .25 | .25 | — |
| Lactic Acid - USP (88%) | .09 | .09 | .09 | — | — | — | — | — | — |
| Acetic Acid | — | — | — | .04 | .04 | .04 | .04 | .04 | — |
| Fragrance | .1 | .1 | .1 | .1 | .1 | .1 | .1 | .1 | — |
| pH | 6.0 | 6.5 | 7.0 | 6.0 | 6.5 | 7.0 | 6.5 | 6.5 | 6.5 |
| Deionized Water | balance to provide 100 percent by weight | | | | | | | | |

TABLE VII

ANTIBACTERIAL EFFICACY SCREEN THIRTY SECOND KILL STUDY AGAINST *Staphylococcus aureus* (ATCC #33591)

| COMPOSITION | LOG REDUCTION |
|---|---|
| 21 | 2.9452 |
| 22 | 4.8610 |
| 23 | >5.4631 |
| 24 | 2.9466 |
| 25 | 4.4631 |
| 26 | >5.4631 |
| 27 | 3.7388 |
| 28 | 3.4993 |
| 29 (control) | 0.8099 |

As can be seen in the Table VII, the specific type of acid modifier employed had little, if any, effect on the antibacterial performance of the compositions. However, the pH of the compositions does appear to a least partially effect the antibacterial activity of the compositions. However, as compared to the control composition (Composition 29) it is clear that the compositions of the present invention provide far better antibacterial properties. When no APG or amphoteric surfactant are employed, the efficacy log reduction was found to be only about 0.80, a factor of 4 or 5 times less than that of the compositions of the present invention. Thus, it should be evident that the relatively mild compositions of the present invention are effective in destroying bacteria as well as or even better than compositions which do not include APG or amphoteric surfactants, even when different acid modifiers are used or at different pH.

Still further, three more compositions (30 through 32, inclusive) were prepared using all of the essential ingredients of the present invention and according to the present invention as detailed hereinabove. Specifically, as shown in Table VIII, the compositions again included a soluble salt of (ethylene glycol distearate pearl) were also added. The pH of each composition was adjusted with lactic acid to about 7.0, and the balance of the composition was water to provide 100 percent by weight of the total composition.

For these compositions, blends of APG were used to determine what effect, if any, they would have on the challenge bacteria. Composition 30 was generally a control and included 100 percent APG-200. Composition 31 was a 75/25 blend of APG-200/APG-400, and Composition 32 was a 25/75 blend of APG-200/APG-400.

Table IX reports the efficacy in terms of log reduction for three separate thirty-second kill studies performed against the challenge bacteria, *Staphylococcus aureus* (ATCC Accession No. 33591), *Serratia marcescens* (ATCC Accession No. 14756), and *Pseudomonas cepacia* (an in-house isolate of bacteria).

TABLE VIII

ANTIMICROBIAL EFFICACY SCREEN OF APG 200/APG 400 BLENDS IN THE CHG ANTIMICROBIAL FORMULATIONS THIRTY SECOND EXPOSURE KILL STUDY

| | COMPOSITION (PERCENT BY WEIGHT) | | |
|---|---|---|---|
| INGREDIENT {trademane} | 30 | 31 | 32 |
| Chlorhexidene Gluconate (20% active) | 2 | 2 | 2 |
| Hydroxyethylcellulose {Natrosol 250 HHR} | .8 | .8 | .8 |
| Propylene Glycol-USP | 3 | 3 | 3 |
| APG-200 (65% active) | 6 | 4.5 | 1.5 |
| APG-400 (50% active) | 0 | 1.5 | 4.5 |
| Cocobetaine ($C_{12-14}$ alkylammonio carboxylate) {Mackam CB-35} (35% active) | 2 | 2 | 2 |
| Cocoamidopropyl phosphatidyl PG-dimonium chloride {Phospholipid PTC} (47% active) | .25 | .25 | .25 |
| Lactic Acid to pH 7.0 (88%) | .25 | .25 | .25 |
| Dimethyl Oxazolidine {oxaban A} | .05 | .05 | .05 |

TABLE VIII-continued

ANTIMICROBIAL EFFICACY SCREEN OF APG 200/APG 400 BLENDS IN THE CHG ANTIMICROBIAL FORMULATIONS THIRTY SECOND EXPOSURE KILL STUDY

| INGREDIENT {tradename} | COMPOSITION (PERCENT BY WEIGHT) | | |
|---|---|---|---|
| | 30 | 31 | 32 |
| Ethylene glycol distearate pearl | .1 | .1 | .1 |
| Fragrance | .1 | .1 | .1 |
| Deionized Water | balance to provide 100 percent by weight | | |

TABLE IX

ANTIBACTERIAL EFFICACY SCREEN OF APG 200/APG 400 BLENDS IN THE CHG ANTIMICROBIAL FORMULATIONS OF TABLE VIII THIRTY SECOND EXPOSURE KILL STUDY

| CHALLENGE MICROBE | LOG REDUCTION | | |
|---|---|---|---|
| | 30 | 31 | 32 |
| *Staphylococcus aureus* (ATCC 33591) | >5.4370 | 5.4370 | >5.4370 |
| *Serratia marcescens* (ATCC 14756) | >5.6735 | >5.6735 | 4.5596 |
| *Pseudomonas cepacia* (in-house isolate) | >5.0000 | ≈5.0000 | ≈2.9646 |

As can be seen in Table IX, the ratio of APG-200 to APG-400 used had little effect on the two commonly found bacteria *Staphylococcus aureus* and *Serratia marcescens*, while the 25/75 blend of APG-200/APG-400 was noted as less effective on the in-house isolate *Pseudomonas cepacia*. Nevertheless, it is believed that these results indicate that a blend of APGs can be employed in the composition of the present invention without destroying the antimicrobial activity of the chlorhexidine.

In the next two compositions produced to the present invention, differing ratios of APG-200 to APG-400 were blended, and the efficacy of the compositions were tested against 16 different strains of bacteria. In particular, the compositions (33 and 34, respectively) included essentially the same ingredients in the same amounts as noted hereinabove for Compositions 30–32. However, this time, Composition 33 included an 85/15 blend ratio of AGP-200 to APG-400 while Composition 34 included a 75/25 blend ratio of APG-200 to APG-400.

Table X hereinbelow presents the compositional formulations of both of the Compositions 33 and 34, and Table XI reports the efficacy results in terms of log reduction for thirty-second kill studies performed against the 16 different strains of challenge bacteria.

TABLE X

ANTIMICROBIAL CLEANSING FORMULATIONS

| INGREDIENT {tradename} | COMPOSITION (PERCENT BY WEIGHT) | |
|---|---|---|
| | 33 | 34 |
| Chlorhexidene Gluconate (20% active) | 2 | 2 |
| Hydroxyethylcellulose {Natrosol 250 HHR} | .8 | .8 |
| Propylene Glycol-USP | 3 | 3 |
| APG-200 (65% active) | 5.1 | 4.5 |
| APG-400 (50% active) | 0.9 | 1.5 |

TABLE X-continued

ANTIMICROBIAL CLEANSING FORMULATIONS

| INGREDIENT {tradename} | COMPOSITION (PERCENT BY WEIGHT) | |
|---|---|---|
| | 33 | 34 |
| Cocobetaine ($C_{12-14}$ alkylammonio carboxylate) {Mackam CB-35} (35% active) | 2 | 2 |
| Polyoxyethylene (8) Linear $C_{9-11}$ alkanol (Linear $C_{9-11}$ alcohol ethoxylate {EO = 8}) | 1 | 1 |
| Cocoamidopropyl phosphatidyl PG-dimonium chloride {Phospholipid PTC} (47% active) | .25 | .25 |
| Lactic Acid to pH 7.0 (88%) | .27 | .27 |
| Dimethyl Oxazolidine {Oxaban A} | .07 | .07 |
| Ethylene glycol distearate pearl | .1 | .1 |
| Fragrance | .1 | .1 |
| Deionized Water | balance to provide 100 percent by weight | |

TABLE XI

ANTIMICROBIAL EFFICACY STUDY OF THE NEW CHG ANTIMICROBIAL FORMULATIONS OF TABLE X

| CHALLENGE MICROBE (ATCC Strain) | COMPOSITION LOG REDUCTION | |
|---|---|---|
| | 33 | 34 |
| *Staphylococcus aureus* (ATCC 33591) | >5.3747 | >5.3747 |
| *Staphylococcus aureus* (ATCC 6538) | >5.1319 | >5.1319 |
| *Staphylococcus aureus* (ATCC 25923) | 4.6297 | 4.9754 |
| *Staphylococcus epidermidis* (ATCC 14990) | >4.7443 | >4.7443 |
| *Serratia marcescens* (ATCC 14756) | >5.4949 | >5.4949 |
| *Escherichia coli* (ATCC 8739) | >5.2607 | >5.2607 |
| *Salmonella typhimurium* (ATCC 14028) | >5.1319 | >5.1319 |
| *Shigella sonnei* (ATCC 11060) | >5.5244 | >5.5244 |
| *Proteus mirabilis* (ATCC 7002) | >5.2330 | >5.2330 |
| *Klebsiella ozaenae* (ATCC 11296) | >5.17456 | >5.17456 |
| *Listeria monocytogenes* (ATCC 7644) | >4.3522 | >4.3522 |
| *Enterococcus faecium* (ATCC 19434) | >4.5378 | >4.5378 |
| *Pseudomonas aeruginosa* (ATCC 9027) | >5.1139 | 5.1037 |
| *Pseudomonas aeruginosa* (ATCC 15442) | 4.9786 | 4.5779 |
| *Pseudomonas cepacia* (ATCC 25416) | 5.1729 | >5.2301 |
| *Pseudomonas cepacia* (in-house isolate) | 4.6490 | 4.7951 |

As seen in Table XI, compositions 33 and 34 were very effective against all 16 challenge bacteria based upon an average log reduction of three separate trials performed against each bacteria. In fact, composition 34 is one of the most preferred compositions of the present invention in view of its antimicrobial efficacy.

Finally, six additional compositions (35 through 40, inclusive) were prepared according to the concepts of the present invention. Each of these compositions are seen as preferred for the present invention. Of course, it will be appreciated that other additives such as a fragrance, coloring agent, opacifying agent, pearlizing agent, vitamins or other additives which would not materially affect the composition may be added to these subject compositions without departing from the spirit of the invention. The compositional formulations of each of these compositions are present in Table XII hereinbelow.

TABLE XII

ANTIMICROBIAL CLEANSING COMPOSITIONS

| INGREDIENT {tradename} | COMPOSITION (percent by weight) | | | | | |
|---|---|---|---|---|---|---|
| | 35 | 36 | 37 | 38 | 39 | 40 |
| Chlorhexidine Gluconate (20% active) | 2 | 2 | 2 | 2 | 2 | 2 |
| Hydroxyethyl cellulose {Natrosol 250 HHR} | 0.8 | 0.8 | 0.8 | 0.8 | 0.8 | 0.8 |
| Propylene Glycol-USP | 3 | 3 | 3 | 3 | 3 | 3 |
| Alkyl polyglucoside (50% active) | 6 | 6 | 6 | 6 | 6 | 6 |
| Cocobetaine (35% active) ($C_{12-14}$ alkylammonio carboxylate) {Mackam CB-35} | 2 | — | — | 1–2 | 1–2 | 2 |
| Polyoxyethylene (10) tridecanol (Tridecylalcohol ethoxylate [EO = 10]) {Rhoadsurf BC-720} | — | –3 | — | 1–3 | — | — |
| Polyoxyethylene (8) Linear $C_{9-11}$ alkanol (Linear $C_{9-11}$ alcohol ethoxylate [EO = 8]) {Neodol 91-8} | — | — | 1–3 | — | 1–3 | — |
| Cocoamidopropyl PG dimonium chloride phosphate {phospholipid PTC} (47% active) | 0.25 | 0.25 | 0.25 | 0–1 | 0.25 | 0.25 |
| Lactic Acid - USP [88%] to pH 7.0 | 0.24 | 0.24 | 0.24 | 0.24 | 0.24 | 0.25 |
| Dimethyl Oxazolidine {Oxaban A} | 0.05 | 0.05 | 0.05 | 0.05 | 0.05 | 0.05 |
| Ethylene glycol distearate peral | — | — | — | — | — | 0.5 |
| Deionized Water | balance to provide 100 percent by weight | | | | | |

Results of an in vivo glove-juice study performed against *Serratia marcescens* (Accession No. 14756) are presented hereinbelow in Table XIII. In this test, about five milliliters (5 ml) aliquots of approximately $10^8$/ml *Serratia marcescens* were pipetted into each human subject's cupped hands. The inoculum was then distributed evenly over both hands and part of the forearm by gentle massage. After one minute to air dry, the subject's hands were washed with the antimicrobial composition of the present invention and rinsed. Excess water was shaken from the hands and powder-free sterile gloves were placed over the hands. A sterile solution was instilled into each glove, and the wrists of the subject were secured. An attendant massaged the hands through the gloves in a standardized manner for about 60 seconds. Aliquots of the glove juice were removed and serially diluted in a tryptic soy broth (TSB). Duplicate spread plates were prepared from each dilution using tryptic soy agar (TSA). The plates were incubated at 20°–25° C. for approximately 48 hours, and plates having 25–250 colony forming units were counted. This procedure was repeated ten times with a minimum of five minutes between applications and washings. The log reduction from the baseline (0 washes) and log bacterial populations after 0, 1, 5 and 10 washes are provided in Table XIII hereinbelow. It can be seen that, based upon the log reduction values obtained for these compositions, the present invention is effective in destroying bacteria and other microorganisms, while at the same time, is mild to the skin.

TABLE XIII

IN VIVO GLOVE-JUICE STUDY PREFORMED AGAINST *SERRATIA MARCESCENS*

| SUBJECT | BASELINE | WASH #1 | WASH #5 | WASH #10 |
|---|---|---|---|---|
| 2 | 8.54 | 5.76 | 4.59 | 3.87 |
| 5 | 7.12 | 6.43 | 4.57 | 4.45 |
| 9 | 7.69 | 5.90 | 4.89 | 4.75 |
| Mean $Log_{10}$ Bacterial Populations | 7.78 | 6.03 | 4.68 | 4.36 |
| Mean Log Reduction from Baseline | | 1.75 | 3.10 | 3.42 |

An additional 15 washes were made to determine the potential for skin irritation. After 25 total washes, skin irritation was found to be negligible.

Thus it should be evident that the compositions of the present invention are highly effective in killing bacteria and other microorganisms while maintaining low skin irritation. The invention is particularly suited for hospital operating and surgical staff and other health care givers, but is not necessarily limited thereto. The compositions of the present invention can also be used with other surfactants or other ingredients including but not limited to fragrances, perfumes, coloring agents, preservatives, opacifying agents, pearlizing agents, vitamins, fungicides, thickeners, antioxidants, emollients, skin care additives, other foaming agents, and the like, which do not materially effect the cleansing and disinfecting nature of the composition.

Based upon the foregoing disclosure, it should now be apparent that the use of the composition described herein will carry out the objects set forth hereinabove. It is, therefore, to be understood that any variations evident fall within the scope of the claimed invention and thus, the selection of specific component elements can be determined without departing from the spirit of the invention herein disclosed and described. In particular and as noted hereinabove, nonionic surfactants according to the present invention are not necessarily limited to those presented in the Examples. Any APG or alcohol ethoxylate which, when added to a composition according to the present invention, provides a composition which can be shown to exhibit a log reduction value of at least 3 and preferably at least 5, is believed suitable for the present invention. Moreover, as noted hereinabove, other viscosifiers and thickeners can be substituted for the hydroxyethyl cellulose. This, the scope of the invention shall include all modifications and variations that may fall within the scope of the attached claims.

What is claimed is:

1. An antimicrobial cleansing composition comprising:
   an effective amount of a salt of chlorhexidine for providing antimicrobial activity to the cleansing composition;
   an amount of at least one alkyl polyglucoside effective for not substantially reducing the antimicrobial activity of said salt of chlorhexidine; and
   an amphoteric surfactant selected from the group consisting of an alkyl phosphatidyl propylene glycol-dimonium chloride and an alkylammino carboxylate wherein in the alkyl group is 8 to 18 carbon atom in an amount effective for providing foaming properties;
   said composition being devoid of any polyoxypropylene/polyoxyethylene block copolymers, any lower alkanols, and any alcohol diluents, and wherein said composition exhibits at least about a log 3 reduction against a bacteria selected from the group consisting of *Staphylococcus aureus* (ATCC #33591), *Enterococcus faecium* (ATCC #19434), *Serratia marcescens* (ATCC 14756), *Escherichia coli* (ATCC 8739), *Pseudomonas aeruginosa* (ATCC 15442) in a 30 second exposure kill test.

2. An antimicrobial cleansing composition, as set forth in claim 1, wherein said salt of chlorhexidine is gluconate, acetate, formate, lactate, isethionate, succinamate, glutamate, mono-diglycollate, dimethanesulfonate, di-isobutyrate, or glucoheptonate.

3. An antimicrobial cleansing composition, as set forth in claim 2, wherein said salt is chlorhexidine digluconate.

4. An antimicrobial cleansing composition, as set forth in claim 1, wherein said alkyl polyglucoside has an alkyl chain length of from about $C_8$ to about $C_{16}$.

5. An antimicrobial cleansing composition, as set forth in claim 1, further comprising a non-aromatic alcohol ethoxylate selected from the group consisting of linear $C_{9-11}$ alcohol ethoxylate (EO=8), linear $C_{9-11}$ alcohol ethoxylate (EO=6), linear $C_{10}$ alcohol ethoxylate (EO=4), linear $C_{10}$ alcohol ethoxylate (EO=6), and linear $C_{8-10}$ alcohol ethoxylate (EO=2); and said alkyl polyglucoside.

6. An antimicrobial cleansing composition, as set forth in claim 5, wherein said alcohol ethoxylate is a branched alcohol ethoxylate having less than 14 carbon atoms.

7. An antimicrobial cleansing composition, as set forth in claim 1, wherein said alkylammonio carboxylate having from 8 to 18 carbons atoms is cocobetaine.

8. An antimicrobial cleansing composition, as set forth in claim 1, further comprising a polymeric viscosifier.

9. An antimicrobial cleansing composition, as set forth in claim 8, wherein said polymeric viscosifier includes hydroxyethyl cellulose.

10. An antimicrobial cleansing composition, as set forth in claim 1, further comprising an acid to adjust the pH of the composition.

11. An antimicrobial cleansing composition, as set forth in claim 10, wherein said acid is selected from the group consisting of lactic acid, acetic acid, glycolic acid, citric acid, and gluconic acid.

12. An antimicrobial cleansing composition, as set forth in claim 1, having a pH between about 5.5 and 8.

13. An antimicrobial cleansing composition, as set forth in claim 1, further comprising a non-alcoholic carrier.

14. An antimicrobial cleansing composition, as set forth in claim 13, wherein said non-alcoholic carrier is water.

15. An antimicrobial cleansing composition, as set forth in claim 1, wherein said salt of chlorhexidine is present in an amount ranging between about 0.2 percent active by weight and about 5 percent active by weight of the total composition.

16. An antimicrobial cleansing composition, as set forth in claim 1, wherein said alkyl polyglucoside is present in an amount ranging from an effective amount for increasing the antimicrobial activity of said salt of chlorhexidine in water to about 10 percent active by weight of the total composition.

17. An antimicrobial cleansing composition, as set forth in claim 1, further comprising at least one additive selected from the group consisting of fragrances, perfumes, coloring agents, opacifying agents, pearlizing agents, vitamins, fungicides, antioxidants, emollients, skin care additives, and foaming agents.

* * * * *